United States Patent [19]

Schäfer et al.

[11] Patent Number: 5,866,716

[45] Date of Patent: Feb. 2, 1999

[54] PROCESS FOR SELECTIVELY PREPARING CARBOXYLIC ACIDS BY CARBONYLATION OF OLEFINS

[75] Inventors: Martin Schäfer, Ludwigshafen; Arthur Höhn, Kirchheim; Ferdinand Lippert, Bad Dürkheim, all of Germany

[73] Assignee: BASF Aktiengesellschaft, Ludwigshafen, Germany

[21] Appl. No.: 697,377

[22] Filed: Aug. 23, 1996

[30] Foreign Application Priority Data

Aug. 23, 1995 [DE] Germany .......................... 19530992.8

[51] Int. Cl.⁶ .................................................. C07C 51/14
[52] U.S. Cl. ............................................................. 562/522
[58] Field of Search ............................................. 562/522

[56] References Cited

U.S. PATENT DOCUMENTS

| | | | |
|---|---|---|---|
| 3,816,490 | 6/1974 | Forster | 260/413 |
| 3,891,683 | 6/1975 | Isa et al. | 260/410.6 |
| 4,588,834 | 5/1986 | Larkin | 560/233 |

FOREIGN PATENT DOCUMENTS

| | | |
|---|---|---|
| 0495547 | 1/1992 | European Pat. Off. . |
| 0495547 | 7/1992 | European Pat. Off. . |
| 2263442 | 7/1973 | Germany . |

OTHER PUBLICATIONS

Industrielle Organische Chemie, 1978, 2nd Edition, Verlag Chemie, p. 132.

Kaneda et al, Chemistry Letters, pp. 1765–1766, 1981.

Fachinetti et al, Inorg. Chem., 1994, 33, No. 8, pp. 1720–1722.

Venalainen et al, Journal of Molecular Catalysts, 34 (1986), pp. 293–303.

*Primary Examiner*—Gary Geist
*Assistant Examiner*—Rosalynd Keys
*Attorney, Agent, or Firm*—John H. Shurtleff

[57] ABSTRACT

A process for selectively preparing a carboxylic acid by reacting an olefin with carbon monoxide in the presence of at least an equimolar amount of water with respect to the olefin at a temperature of from 50° to 150° C. and a pressure of from 30 to 150 bar and also in the presence of a halogen-free catalyst system consisting of rhodium or a rhodium compound and at least one nitrogen-containing heterocyclic compound as a promoter

11 Claims, No Drawings

PROCESS FOR SELECTIVELY PREPARING CARBOXYLIC ACIDS BY CARBONYLATION OF OLEFINS

The present invention relates to a process for selectively preparing carboxylic acids by reacting an olefin with carbon monoxide in the presence of at least an equimolar amount of water and a halogen-free catalyst system, viz. a mixture of rhodium or a rhodium compound and at least one nitrogen-containing heterocyclic compound, at elevated temperature and pressure.

In Industrielle Organische Chemie, 1978, 2nd edition, Verlag Chemie, p. 132, Weissermel et al. describe the carbonylation of olefins by the Reppe process, for example the preparation of propionic acid from ethylene, carbon monoxide and water in the presence of catalysts. The catalyst used is nickel propionate which is converted under the reaction conditions into nickel carbonyl. A high conversion of the carbon monoxide is only achieved at high pressures (from 200 to 240 bar). These reaction conditions make the construction of suitable reactors technically complicated and, owing to the corrosivity of the product under the reaction conditions, require special and expensive materials of construction.

Carbonylations of olefins can be carried out at pressures of about 100 bar using nobel metal catalysts. Thus, EP-A-495 547 discloses catalysts comprising a palladium source and bidentate phosphine ligands. However, such catalysts are frequently deactivated after a short reaction time by precipitation of metallic palladium; in particular, the phosphine ligands are not thermally stable under the desired reaction conditions.

DE-A-21 01 909 relates to a rhodium carbonyl halide catalyst which, without addition of a further halide promoter, converts olefins in the presence of water and CO into carboxylic acids. Good yields and selectivities of a carboxylic acid, for example propionic acid, are obtained with this system only when CO/olefin ratios of greater than 2/1 are employed. Thus, for example, at a molar ratio of CO/ethene of 8/1 and using $[RhCl(CO)_2]_2$ as catalyst, reaction rates of from 233 to 520 g of propionic acid/h/g of Rh are achieved. In contrast, at a CO/ethene ratio of 1/1, the reaction rate is only 105 g of propionic acid/h/g of rhodium. If a halogen-free rhodium catalyst such as $Rh_4(CO)_{12}$ is used, the reaction rate drops to 51 g of propionic acid/h/g of rhodium.

DE-A-22 63 442 (U.S. Pat. No. 3,816,490) discloses a process for preparing carboxylic acids and carboxylic anhydrides from olefins using a halogen-free rhodium or iridium catalyst in the presence of phenol or thiophenol derivatives or fluorinated carboxylic acids, thiocarboxylic acids or sulfonic acids. However, the catalytic activity is comparatively low.

It is an object of the present invention to provide a process for the carbonylation of olefins which avoids the abovementioned disadvantages.

We have found that this object is achieved by a novel and improved process for selectively preparing carboxylic acids from olefins and carbon monoxide in the presence of at least an equimolar amount of water and a halogen-free catalyst system, particularly in the absence of hydrogen halide or a halogen promoter at from 30° to 200° C. and pressures of from 30 to 200 bar, wherein the catalyst system used is a mixture of rhodium or a rhodium compound and at least one nitrogen-containing heterocyclic compound.

Suitable starting materials for the process of the present invention are aliphatic and cycloaliphatic alkenes preferably having from 2 to 20, particularly preferably from 2 to 7, carbon atoms. Examples which may be mentioned are ethylene, propylene, iso-butene, 1-butene, 2-butene and the isomers of pentene and hexene, octene and also cyclopentene, among which ethylene is preferred. These olefins are reacted with water and CO to produce carboxylic acids.

Suitable nitrogen-containing heterocyclic compounds for the process of the present invention are, for example, derivatives of pyridine, quinoline, isoquinoline, pyrimidine, pyridazine, pyrazine, pyrazole, imidazole, thiazole and oxazole, among which the derivatives of pyridine, quinoline and isoquinoline are preferred, the derivatives of pyridine being particularly preferred.

Pyridine derivatives which can be used are pyridine itself and also, for example, compounds which are monosubstituted to trisubstituted by alkyl or aryl, for example picoline, lutidine or collidine. Particularly suitable compounds are pyridine and monosubstituted derivatives such as 3-picoline, 4-picoline, 4-t-butylpyridine, 4-benzylpyridine, 4-(phenylpropyl)pyridine, 4-(pyridylpropyl)pyridine, 4-phenylpyridine and also 2-(pyridyl)ethanesulfonic acid and their salts.

The pyridine derivative can also be bound to an organic or inorganic support. Particularly suitable are polymers or copolymers of 4-vinylpyridine which may be soluble or insoluble in the reaction medium depending on their molecular weight and their degree of crosslinking. In the case of insoluble polymers, the rhodium catalyst can deposit on the support after the carbonylation reaction and can be removed from the reaction mixture by filtration.

Carbon monoxide can be used in pure form or diluted with inert gases such as nitrogen or argon.

The molar ratios of the starting compounds olefin and water can vary within wide limits, but an at least equimolar amount of water is generally used. A larger excess of water, eg. from 2 to 10 mol of water per mole of olefin, can be selected.

The molar ratio of carbon monoxide to olefin can also be varied greatly, eg. from 0.9:1 to 20:1 mol of olefin per mole of carbon monoxide. The preparation of propionic acid is generally carried out at a molar ratio of CO to ethene of preferably from 0.9:1 to 2:1, particularly preferably 1:1.

Catalysts which can be used in the process of the present invention are halogen-free rhodium compounds plus at least one nitrogen-containing heterocyclic compound. To enable the active components of rhodium to be formed, soluble rhodium compounds such as acetates, propionates, acetylacetonates, oxides, hydroxides and carbonates are advantageously added to the reaction mixture. When using a halogen-free rhodium(III) compound as precursor, it may be possible to accelerate the formation of the active catalyst by metering $H_2$ into the reaction mixture. The activation (precarbonylation) of the catalyst can also be carried out in a separate reaction space by reaction with CO and water or with CO and $H_2$ at from 50° to 150° C. and pressures of from 50 to 150 bar. Also suitable are carbonyl compounds such as $Rh(acac)(CO)_2$, $Rh_4(CO)_{12}$, $Rh_6(CO)_{16}$ or salts of the anion $[Rh_{12}(CO)_{30}]^{2-}$ and also rhodium compounds stabilized by donor ligands (eg. nitrogen bases) or olefins.

The rhodium content of the reaction solution is generally from 0.001 to 1% by weight, preferably from 0.005 to 0.5% by weight, particularly preferably from 0.01 to 0.3% by weight, calculated as metal.

As further catalyst component, use is made of at least one, ie. 1, 2, 3, 4, 5, 6, 7, 8 or more, preferably 1, 2, 3, 4 or 5, particularly preferably 1, 2 or 3, in particular 1 or 2, nitrogen-containing heterocyclic compounds. Preference is given to pyridine and pyridine derivatives such as picoline and lutidine. The content of these bases in the reaction mixture is from 1 to 50% by weight, preferably from 10 to 30% by weight.

The molar ratio of the nitrogen-containing heterocyclic compound to rhodium is generally from 10:1 to 10000:1, preferably from 50:1 to 1500:1.

The reaction can be carried out with or without solvent.

If no additional solvent is used, it is preferable to carry out the reaction in a 10–90% strength by weight, preferably 20–70% strength by weight, aqueous solution of the carboxylic acid being prepared. In the preparation of propionic acid, the use of aqueous propionic acid as solvent is preferred.

Apart from aqueous carboxylic acid, suitable solvents are aprotic polar solvents such as acetone, N-methylpyrrolidone and ethers such as diethyl ether, dioctyl ether, diethoxyethane, dioxane, diethylene glycol diethyl ether, diethylene glycol dioctyl ether and high-boiling aliphatic hydrocarbons and aromatic hydrocarbons such as toluene. Depending on the type and amount of solvent used, the reaction mixture can consist of one or two phases.

Preference is given to the use of ethers of the general formula (I)

where $R^1$ and $R^2$ are hydrogen, $C_1$–$C_{20}$-alkyl, aryl,

or $R^1$ and $R^2$ are together a $C_1$–$C_{20}$-alkylene chain $R^3$ is hydrogen, $C_1$–$C_{20}$-alkyl or aryl and n is from 0 to 30, with the proviso that $R^1$ and $R^2$ are not

when n is 0 or 1 and $R^1$ and $R^2$ are not hydrogen when n is 0, as solvents, with the compounds having $R^1$, $R^2$=$C_1$–$C_{20}$-alkyl, in particular ethyl, propyl, butyl, pentyl, hexyl, heptyl, octyl, decyl, ethylhexyl, being particularly preferred. The compounds (I) also include cyclic ethers such as dioxane when the groups $R^1$ and $R^2$ are linked by at least one bond.

The content of additional solvent in the reaction mixture can be varied within a wide range. It is generally from 20 to 80% by weight, preferably from 30 to 60% by weight.

The use of an additional solvent promotes the solubility of the olefin, the carbon monoxide and the active catalyst in the reaction mixture. Thus, for example in the carbonylation of ethene, the use of the ethers described as solvents makes possible the synthesis of propionic acid in high yield and with high selectivity under milder reaction conditions than using propionic acid/water as solvent.

The reaction is generally carried out at from 30° to 200° C., preferably at from 50° to 150° C., and pressures of from 30 to 250 bar. Higher pressures and higher temperatures generally lead to increased formation of by-products such as ketones, alkanes, aldehydes. In the carbonylation of terminal olefins, higher temperatures promote double bond isomerization.

In the synthesis of propionic acid, the reaction is preferably carried out at from 50 to 150 bar; in the synthesis of higher carboxylic acids such as nonanoic acid, it is preferably carried out at from 100 to 250 bar.

The starting compounds olefin, water and the catalyst system can be mixed, if desired in a solvent, in a reactor prior to the reaction. They can then be heated to the reaction temperature and the reaction pressure is set by injecting carbon monoxide or, when using short-chain olefins, by injecting a mixture of this olefin and carbon monoxide.

In general, the reaction is complete after from 0.5 to 3 hours. It can be carried out continuously or batchwise in reactors such as tanks, bubble columns, tube reactors or circulation reactors.

To isolate the process products, the reaction mixture produced is depressurized in a preferred embodiment. The liquid phase of the reaction mixture, which contains soluble or suspended catalyst in addition to the process product, is worked up by distillation, with the process product being isolated with or without a subsequent fine distillation. The catalyst-containing distillation bottoms are returned to the reaction. Likewise, any catalyst constituents separated off prior to the distillation and also volatile catalyst constituents separated off as low boilers or as sidestream of a distillation can be recycled after appropriate work-up.

The active catalyst present in the liquid reaction mixture produced is inactivated prior to the work-up by distillation, if desired by reaction with oxygen or air at from 50° to 150° C. and from 0.5 to 10 bar.

The process of the present invention allows the preparation of the process products under moderate reaction conditions in high space-time yield and at high selectivity.

EXAMPLES

Batchwise experiments for preparing propionic acid

Examples 1 to 20

An autoclave was charged with Rh(acac)(CO)$_2$ and the pyridine derivative in a mixture of propionic acid and water as solvent. A pressure of 30 bar was set using a mixture of 50% by volume of ethene and 50% by volume of CO and the mixture was brought to the appropriate reaction temperature. The desired reaction pressure was then set by injecting the CO/ethene mixture and was maintained by injection of further amounts (every 15 minutes). After 1 hour, the autoclave was depressurized and the reaction mixture produced was analyzed titrimetrically and by gas chromatography. The results are summarized in Table 1.

Abbreviations used:

ResT=residence time, duration of experiment, STY=space-time yield, Sel.=selectivity based on ethene, PA=propionic acid, PAL=propionaldehyde, DEK=diethyl ketone, 4-OHA=4-oxohexanoic acid, py=pyridine, 3-Mepy=3-methylpyridine, 4-Mepy=4-methylpyridine, 4-tBupy=4-tert-butylpyridine, 4-CH$_2$Phpy=4-benzylpyridine, 4-Phpy=4-phenylpyridine, 4-(CH$_2$)$_3$Phpy=(3-phenyl)propylpyridine, 4,4'-py(CH$_2$)$_3$py=4,4'-trimethylenedipyridine, 2,4,6-Me$_3$py=2,4,6-trimethylpyridine.

Comparative Examples 21 to 24

An autoclave was charged with Rh(acac)(CO)$_2$ in a mixture of propionic acid and water as solvent. In Examples 22 and 23, pyridine was added. A pressure of 30 bar was set using a mixture of 50% by volume of ethene and 50% by volume of CO and the mixture was brought to the appropriate reaction temperature. The desired reaction pressure was then set by injecting the CO/ethene mixture and was maintained by injection of further amounts (every 15 minutes). After 1 hour, the autoclave was depressurized and the reaction mixture produced was analyzed titrimetrically and by gas chromatography. The results are summarized in Table 2.

Example 25

An autoclave was charged with 0.08 g of $Rh_2(OAc)_4$ and 10 g of pyridine in a mixture of propionic acid and water as solvent. A pressure of 30 bar was set using a mixture of 50% by volume of ethene and 50% by volume of CO and the mixture was heated to 100° C. The desired reaction pressure was then set by injecting the CO/ethene mixture and was maintained by injection of further amounts (every 15 minutes). After 1 hour, the autoclave was depressurized and the reaction mixture produced was analyzed titrimetrically and by gas chromatography. The results are summarized in Table 3.

Example 26

The procedure of Example 25 was repeated using 0.11 g of $Na_2[Rh_{12}(CO)_{30}]$ and 0.2 g of $NBu_4OH$ as catalyst. The results are summarized in Table 3.

Example 27

An autoclave was charged with 0.22 g of $Rh(OAc)_3$ and 10 g of pyridine in a mixture of propionic acid and water as solvent. The mixture was subsequently heated to 100° C. The desired reaction pressure was then set by injecting the CO/ethene mixture and was maintained by injection of further amounts (every 15 minutes). After 1 hour, the autoclave was depressurized and the reaction mixture produced was analyzed titrimetrically and by gas chromatography. The results are summarized in Table 3.

Example 28

An autoclave was charged with 0.22 g of $Rh(OAc)_3$ and 10 g of pyridine in a mixture of propionic acid and water as solvent. A preliminary pressure of 10 bar was set using a 1/1 mixture of $CO/H_2$. The mixture was subsequently heated to 100° C. The desired reaction pressure was then set by injecting the CO/ethene mixture and was maintained by injection of further amounts (every 15 minutes). After 1 hour, the autoclave was depressurized and the reaction mixture produced was analyzed titrimetrically and by gas chromatography. The results are summarized in Table 3.

Examples 29 to 39

An autoclave was charged with 0.22 g of $Rh(acac)(CO)_2$ and 10 g of the pyridine derivative in a mixture of 50 g of ether and 40 g of water. A pressure of 30 bar was set using a mixture of 50% by volume of ethene and 50% by volume of CO (in the case of Experiment 36, 30 bar of CO were injected as preliminary pressure) and the mixture was brought to the appropriate reaction temperature. The desired reaction pressure was then set by injecting the CO/ethene mixture and was maintained by injection of further amounts (every 15 minutes). After 1 hour, the autoclave was depressurized and the reaction mixture produced was analyzed titrimetrically and by gas chromatography. The results are summarized in Table 4.

Example 40 a) An autoclave was charged with 0.22 g of $Rh(acac)(CO)_2$ and 10 g of a commercially available 4-vinylpyridine polymer (Aldrich, 2% crosslinked) in a mixture of 50 g of propionic acid and 40 g of water. A pressure of 30 bar was set using a mixture of 50% by volume of ethene and 50% by volume of CO (in the case of Experiment 36, 30 bar of CO were injected as preliminary pressure) and the mixture was heated to 100° C. The reaction pressure of 100 bar was then set by injecting the CO/ethene mixture and was maintained by injection of further amounts (every 15 minutes). After 1 hour, the autoclave was depressurized and the reaction mixture produced was analyzed titrimetrically and by gas chromatography. Propionic acid was formed in an STY of 214 g/l/h and with a selectivity of 90%.

b) The polymer present in the reaction mixture produced in a) was filtered off, dried and, without addition of rhodium, reacted with CO/ethene as described under a). Propionic acid was formed in an STY of 208 g/l/h and with a selectivity of 91%.

This experiment demonstrates that the Rh catalyst can be deposited on the pyridine polymer after the reaction, separated from the reaction mixture produced and returned to the reaction with the polymer.

TABLE 1

Carbonylation of ethylene using a rhodium-pyridine catalyst system

| | | Input | | | | | Output | | | | | | |
|---|---|---|---|---|---|---|---|---|---|---|---|---|---|
| Experiment | Base [g] | Rh [ppm] | PA [g] | $H_2O$ [g] | p [bar] | T [°C.] | Ethane Sel. [%] | PAL Sel. [%] | DEK Sel. [%] | 4-OHA Sel. [%] | PA Sel. [%] | PA STY [g/l/h] | Activity g PA/h/g Rh |
| 1 | py [7.5] | 800 | 30 | 62.5 | 100 | 100 | 0.5 | 0.7 | 0.6 | 3.6 | 94.4 | 240 | 273 |
| 2 | py [10] | 800 | 30 | 60 | 100 | 100 | 0.7 | 0.8 | 0.8 | 3.1 | 94.5 | 317 | 361 |
| 3 | py [15] | 800 | 30 | 55 | 100 | 100 | 0.7 | 0.7 | 0.7 | 2.2 | 95.6 | 375 | 427 |
| 4 | py [10] | 800 | 40 | 50 | 100 | 100 | 1.1 | 0.7 | 1.2 | 4.0 | 93.0 | 456 | 518 |
| 5 | py [10] | 800 | 50 | 40 | 110 | 100 | 0.4 | 0.5 | 0.7 | 5.0 | 93.2 | 581 | 662 |
| 6 | py [10] | 800 | 50 | 40 | 100 | 110 | 1.3 | 0.8 | 2.3 | 3.1 | 89.8 | 420 | 402 |
| 7 | py [10] | 800 | 50 | 40 | 100 | 90 | 0.2 | 0.5 | 0.2 | 5.7 | 96.0 | 369 | 421 |
| 8 | py [10] | 800 | 50 | 40 | 80 | 100 | 0.7 | 0.5 | 0.9 | 4.9 | 93.7 | 279 | 318 |
| 9 | py [10] | 800 | 50 | 40 | 100 | 100 | 0.7 | 0.6 | 0.9 | 4.2 | 93.3 | 422 | 480 |
| 10 | 3-Mepy [10] | 800 | 50 | 40 | 100 | 100 | 1.3 | 0.8 | 2.1 | 6.5 | 89.3 | 337 | 383 |
| 11 | 4-Mepy [10] | 800 | 40 | 50 | 100 | 100 | 0.7 | 0.8 | 0.7 | 3.2 | 94.3 | 358 | 407 |
| 12 | 4-tBupy [10] | 800 | 40 | 50 | 100 | 100 | 1.0 | 1.0 | 4.7 | 4.8 | 88.5 | 442 | 503 |
| 13 | 4-$CH_2$Phpy [10] | 800 | 40 | 50 | 100 | 100 | 1.1 | 0.8 | 2.7 | 5.0 | 90.0 | 397 | 452 |
| 14 | 4-Phpy [10] | 800 | 40 | 50 | 100 | 100 | 0.3 | 0.7 | 1.3 | 4.0 | 93.0 | 384 | 438 |
| 15 | 4-$(CH_2)_3$Ph [10] | 800 | 40 | 50 | 100 | 100 | 0.3 | 0.4 | 0.9 | 4.6 | 93.1 | 279 | 318 |

TABLE 1-continued

Carbonylation of ethylene using a rhodium-pyridine catalyst system

| Experiment | Base [g] | Rh [ppm] | PA [g] | H$_2$O [g] | p [bar] | T [°C.] | Ethane Sel. [%] | PAL Sel. [%] | DEK Sel. [%] | 4-OHA Sel. [%] | PA Sel. [%] | PA STY [g/l/h] | Activity g PA/h/g Rh |
|---|---|---|---|---|---|---|---|---|---|---|---|---|---|
| 16 | 4,4'-py(CH$_2$)$_3$py [10] | 800 | 40 | 50 | 100 | 100 | 0.9 | 0.5 | 0.9 | 4.0 | 93.1 | 384 | 483 |
| 17 | py [5],4-Mepy [5] | 400 | 50 | 40 | 100 | 100 | 0.3 | 0.6 | 1.3 | 6.6 | 91.0 | 355 | 808 |
| 18 | py [5],2,4,6-Me$_3$py[5] | 400 | 50 | 40 | 100 | 100 | 0.3 | 0.6 | 1.7 | 8.8 | 88.5 | 344 | 783 |
| 19 | py [10] | 400 | 50 | 40 | 100 | 100 | 0.6 | 0.7 | 1.4 | 6.5 | 90.8 | 331 | 750 |
| 20 | py [10] | 200 | 50 | 40 | 100 | 100 | 0.5 | 0.9 | 1.3 | 9.6 | 87.6 | 232 | 968 |

TABLE 2

Comparative Examples

| Experiment | Base [g] | Rh [ppm] | PA [g] | H$_2$O [g] | p [bar] | T [°C.] | ResT [h] | Ethane Sel. [%] | PAL Sel. [%] | DEK Sel. [%] | 4-OHA Sel. [%] | PA Sel. [%] | PA STY [g/l/h] | Activity g PA/h/g Rh |
|---|---|---|---|---|---|---|---|---|---|---|---|---|---|---|
| 20 | — | 400 | 60 | 40 | 100 | 150 | 2 | 3.6 | 3.7 | 72.3 | 1) | 20.4 | 31 | 78 |
| 21 | py [1] | 400 | 60 | 40 | 100 | 150 | 1 | 2.5 | 2.2 | 55.2 | 1) | 40.1 | 73 | 183 |
| 22 | py [5] | 400 | 60 | 40 | 100 | 150 | 1 | 6.4 | 3.4 | 26.9 | 1) | 61.4 | 160 | 408 |
| 23 | — | 400 | 60 | 40 | 100 | 125 | 1 | 3.0 | 6.3 | 60.5 | 1) | 31.5 | 12 | 30 |
| 24 | — | 400 | 60 | 40 | 100 | 100 | 1 | 0.1 | 8.3 | 20.2 | 1) | 66.7 | 5 | 13 |

[1] 4-oxohexanoic acid was not analyzed

TABLE 3

Various rhodium complexes as catalyst precursors (p = 100 bar, T = 100° C., 10 g py)

| Experiment | Complex | Rh [ppm] | PA [g] | H$_2$O [g] | p [bar] | T [°C.] | ResT [h] | Ethane Sel. [%] | PAL Sel. [%] | DEK Sel. [%] | 4-OHA Sel. [%] | PA Sel. [%] | PA STY [g/l/h] | Activity g PA/h/g Rh |
|---|---|---|---|---|---|---|---|---|---|---|---|---|---|---|
| 25 | Rh$_2$(OAc)$_4$ | 360 | 60 | 30 | 100 | 100 | 1 | 0.3 | 0.4 | 0.2 | 5.5 | 93.5 | 155 | 430 |
| 26 | Na$_2$[Rh$_{12}$(CO)$_{30}$] | 600 | 50 | 40 | 100 | 100 | 1 | 0.6 | 0.9 | 1.2 | 3.4 | 93.7 | 410 | 683 |
| 27 | Rh(OAc)$_3$ | 800 | 40 | 50 | 100 | 100 | 1 | 0.1 | 0.5 | — | 15.0 | 84.5 | 48 | 55 |
| 28 | Rh(OAc)$_3$[1] | 800 | 40 | 50 | 100 | 100 | 1 | 1.3 | 8.4 | 1.2 | 4.8 | 85.2 | 228 | 281 |

[1] The reaction solution was heated under a CO/H$_2$ preliminary pressure of 10 bar

TABLE 4

Use of ethers as a solvent ([Rh] = 800 ppm, [ether] = 50 g)

| Experiment | Ether [50 g] | Base [10 g] | H$_2$O [g] | p [bar] | T [°C.] | Ethane Sel. [%] | PAL Sel. [%] | DEK Sel. [%] | 4-OHA Sel. [%] | PA Sel. [%] | PA STY [g/l/h] | Activity g PA/h/g Rh |
|---|---|---|---|---|---|---|---|---|---|---|---|---|
| 29 | Diethyl ether | py | 40 | 90 | 90 | 0.04 | 0.4 | 0.0 | 2.5 | 97.0 | 275 | 314 |
| 30 | Di-n-butylether | py | 40 | 90 | 90 | 0.3 | 0.3 | 0.7 | 1.3 | 98.0 | 493 | 561 |
| 31 | Di-n-octyl ether | py | 40 | 90 | 90 | 0.2 | 0.1 | 0.1 | 1.2 | 98.0 | 337 | 384 |
| 32 | Dioxane | py | 40 | 90 | 90 | 0.1 | 1.2 | 0.0 | 4.8 | 93.9 | 228 | 259 |
| 33 | Diethylene glycol diethyl ether | py | 40 | 90 | 90 | 0.1 | 0.6 | 0.0 | 3.9 | 95.5 | 347 | 395 |
| 34 | Diethylene glycol di-n-butyl ether | py | 40 | 90 | 90 | 0.2 | 0.5 | 0.6 | 4.7 | 94.2 | 503 | 573 |
| 35 | Diethylene glycol distearate | py | 40 | 90 | 90 | 2.0 | 0.7 | 1.5 | 4.6 | 91.0 | 418 | 475 |
| 36[1] | Diethylene glycol | py | 40 | 80 | 90 | 0.1 | 0.6 | 0.0 | 0.0 | 99.3 | 154 | 175 |

TABLE 4-continued

Use of ethers asa solvent ([Rh] = 800 ppm, [ether] = 50 g)

| | Input | | | | | Output | | | | | | |
|---|---|---|---|---|---|---|---|---|---|---|---|---|
| Experiment | Ether [50 g] | Base [10 g] | $H_2O$ [g] | p [bar] | T [°C.] | Ethane Sel. [%] | PAL Sel. [%] | DEK Sel. [%] | 4-OHA Sel. [%] | PA Sel. [%] | PA STY [g/l/h] | Activity g PA/h/g Rh |
| 37 | Diethylene glycol di-n-butyl ether | 4-Mepy | 40 | 90 | 90 | 0.2 | 0.5 | 0.4 | 3.4 | 95.4 | 364 | 415 |
| 38 | Diethylene glycol di-n-butyl ether | 4-$(CH_2)_3$py | 40 | 90 | 90 | 0.1 | 0.4 | 0.3 | 3.3 | 95.8 | 352 | 401 |
| 39 | Diethylene glycol di-n-butyl ether | 4-Phpy | 40 | 90 | 90 | 0.1 | 0.4 | 0.0 | 3.3 | 96.2 | 344 | 392 |

[1])This experiment was carried out using a CO/ethene ratio of 2/1.

Experiment 41

An autoclave was charged with 0.1 g of Rh(acac)$(CO)_2$, 20 g of pyridine and 10 g of 1-octene in a mixture of 60 g of propionic acid and 10 g of water as solvent. A pressure of 30 bar was set using CO and the mixture was heated to 100° C. A reaction pressure of 100 bar was then set by injecting CO and was maintained by injection of further amounts (every 15 minutes). After 1 hour, the autoclave was depressurized and the reaction mixture produced was analyzed titrimetrically and by gas chromatography. Nonanoic acid (n/iso 2.6:1) was formed in an STY of 46 g/l/h (Sel.>95%). Nonanal (n/iso) could be detected in traces by gas chromatography. Hydrogenation products such as octane or nonanol were not found.

Experiment 42

An autoclave was charged with 0.55 g of Rh(acac)$(CO)_2$, 10 g of 4-methylpyridine and 20 g of 1-octene in a mixture of 50 g of diethylene glycol di-n-butyl ether and 10 g of water. A pressure of 30 bar was set using CO and the mixture was heated to 90° C. A reaction pressure of 150 bar was then set by injecting CO and was maintained by injecting further amounts (every 15 minutes). After 1 hour, the autoclave was depressurized and the reaction mixture produced was analyzed titrimetrically and by gas chromatography. Nonanoic acid (n/iso=3.8:1) was formed in an STY of 135 g/l/h (Sel.>95%). Nonanal (n/iso) could be detected in traces by gas chromatography. Hydrogenation products such as octane or nonanol were not found.

Continuous experiments

Examples 43 to 48

A mixture of propionic acid, water, pyridine and Rh(acac)$(CO)_2$ was reacted continuously at 100° C. and 100 bar with CO and ethene. After residence times of from 0.5 to 2.1 hours, reaction mixture was continuously taken off and analyzed. The results of these experiments are summarized in Table 5.

Example 49

A mixture of diethylene glycol di-n-butyl ether, water, pyridine and Rh(acac)$(CO)_2$ was reacted continuously at 100° C. and 100 bar with CO and ethene. After a residence time of 2.7 hours, reaction mixture was continuously taken off and analyzed. The result of this experiment is summarized in Table 5.

TABLE 5

Continuous experiments on ethylene carbonylation

| | Input | | | | | Conversion | | | | Output | | | | | | |
|---|---|---|---|---|---|---|---|---|---|---|---|---|---|---|---|---|
| Ex. | Rh [%] | py [%] | PA [%] | $H_2O$ [%] | $C_2H_4$ ratio | $(C_2H_4)$ [%] | ResT [h] | p [bar] | T [°C.] | Ethane Sel. [%] | PAL Sel. [%] | DEK Sel. [%] | 4-OHA Sel. [%] | PA Sel. [%] | PA STY [g/l/h] | Activity g PA/h/g Rh |
| 43 | 0.30 | 22.9 | 13.1 | 64.2 | 1:1 | 84 | 2.1 | 100 | 100 | 0.5 | 0.4 | 1.2 | 2.7 | 95.0 | 475 | 327 |
| 34 | 0.25 | 18.3 | 14.3 | 66.9 | 1.5:1 | 90 | 1.2 | 100 | 100 | 0.4 | 0.9 | 0.3 | 3.8 | 94.5 | 511 | 247 |
| 45 | 0.25 | 18.3 | 14.3 | 66.9 | 2:1 | 87 | 1.2 | 100 | 100 | 0.4 | 0.9 | 0.2 | 3.0 | 95.5 | 493 | 236 |
| 46 | 0.17 | 45.6 | 22.9 | 31.1 | 1.1 | 91 | 0.5 | 100 | 100 | 1.5 | 0.5 | 1.1 | 4.1 | 93.5 | 1225 | 385 |
| 47 | 0.08 | 46.1 | 22.9 | 31.1 | 1.5:1 | | 2.6 | 90 | 100 | 0.2 | 0.6 | 0.03 | 2.1 | 97.0 | 384 | 1280 |
| 48 | 0.20 | 21.0 | 13.5 | 65.1 | 1.1:1 | 98 | 2.0 | 100 | 100 | 0.3 | 0.7 | 0.6 | 4.6 | 93.8 | 574 | 586 |
| | | | | Ether [%] | | | | | | | | | | | | |
| 49 | 0.08 | 15.3 | 38.7 | 45.9 | 1.5:1 | 88 | 2.7 | 90 | 90 | 0.5 | 0.2 | 0.1 | 2.4 | 96.2 | 299 | 1030 |

Continuous experiments on catalyst recycling

Example 50

In a carbonylation reactor, carbon monoxide was reacted continuously at 100° C. and 100 bar with ethene (CO/$C_2H_4$=1.1/1) and water using rhodium and pyridine as catalysts in aqueous propionic acid to give propionic acid. After a residence time of 2 hours, a reaction mixture having the composition 68% of PA, 18% of $H_2O$, 11% of py, 3.3% of 4-OHA, 0.2% of PAL, 0.02% of DEK, 0.23% of Rh was taken off continuously at the top of the reactor. To passivate the rhodium catalyst, the liquid reaction mixture produced was reacted at 100° C. and 3 bar with air in an oxidation reactor (ResT=0.5 hour). Subsequently, the product and by-products as well as water and part of the pyridine were separated off at 150° C. and 0.5 bar in a Sambay evaporator. The rhodium-containing bottoms, which contained 4-oxohexanoic acid as well as pyridine and propionic acid, were treated with CO and returned to the carbonylation reactor. The pyridine discharged at the top of the Sambay evaporator was supplemented continously and metered into the carbonylation reactor together with fresh water and propionic acid. The experiment was carried out for a period of 70 hours and gave propionic acid in an STY of 350 g/l/h and with a Sel. of 95% (Sel.(4-OHA)=3%, Sel.(DEK)=0.1%, Sel.(PAL)=0.9%, Sel.($C_2H_6$)=0.2%). The ethene conversion was 99%.

From the Sambay condensate (composition: 67% of PA, 24% of $H_2O$, 6.5% of py, 1.4% of 4-OHA, 0.4% of PAL, 0.05% of DEK), propionic acid having a purity of $\geq 98.5\%$ can be obtained by distillation. Pyridine is obtained as a high-boiling azeotrope with propionic acid and can be returned to the reaction.

We claim:

1. A process for selectively preparing a carboxylic acid by reacting an olefin with carbon monoxide in the presence of at least an equimolar amount of water with respect to the olefin at a temperature of from 50° to 150° C. and a pressure of from 30 to 150 bar and also in the presence of a halogen-free catalyst system consisting of rhodium or a rhodium compound and at least one nitrogen-containing heterocyclic compound as a promoter.

2. A process as claimed in claim 1, wherein said nitrogen-containing heterocyclic compound and said rhodium or rhodium compound are used in a molar ratio of from 10000:1 to 10:1.

3. A process as claimed in claim 1, wherein the content of said nitrogen-containing heterocyclic compound in the reaction solution is from 1 to 30% by weight.

4. A process as claimed in claim 1, wherein the content of said nitrogen-containing heterocyclic compound used is pyridine, a derivative thereof or their mixtures.

5. A process as claimed in claim 1, wherein the reaction is carried out in an aprotic polar solvent.

6. A process as claimed in claim 5, wherein said aprotic polar solvent is. an ether of the formula I

wherein $R^1$ and $R^2$ taken alone are hydrogen, $C_1$–$C_{20}$-alkyl, aryl,

or $R^1$ and $R^2$ taken together represent a $C_1$–$C_{20}$-alkyl chain, $R^3$ is hydrogen, $C_1$–$C_{20}$-alkyl or aryl and n is an integer from 0 to 30, with the proviso that $R^1$ and $R^2$ are not

when n is 0 or 1 and $R^1$ and $R^2$ are not hydrogen when n is 0.

7. A process as claimed in claim 1, wherein the reaction is carried out in a 10–90% strength by weight aqueous solution of a carboxylic acid as a solvent.

8. A process as claimed in claim 1, wherein the carbon monoxide and the olefin are used in a molar ratio of from 0.9:1 to 20:1.

9. A process as claimed in claim 1, wherein the olefin used is ethylene.

10. A process as claimed in claim 9, wherein the carbon monoxide and the ethylene are used in a molar ratio of from 0.9:1 to 1.2:1.

11. A process as claimed in claim 1, wherein the reaction is carried out in the absence of hydrogen halide or a halogen promoter.

* * * * *